United States Patent
Mejia

(10) Patent No.: US 6,690,968 B2
(45) Date of Patent: Feb. 10, 2004

(54) METHOD OF AND APPARATUS FOR IDENTIFYING A PORTION OF A WAVEFORM REPRESENTING A PHYSIOLOGICAL EVENT

(75) Inventor: Claudio P. Mejia, Stafford, TX (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/974,228

(22) Filed: Oct. 10, 2001

(65) Prior Publication Data

US 2002/0016549 A1 Feb. 7, 2002

Related U.S. Application Data

(62) Division of application No. 09/474,592, filed on Dec. 29, 1999.

(51) Int. Cl.$^7$ .............................................. A61B 5/0456
(52) U.S. Cl. ....................................................... 600/513
(58) Field of Search ...................... 607/23, 24; 600/513, 600/526, 527, 481, 483, 489, 493

(56) References Cited

U.S. PATENT DOCUMENTS

| | | |
|---|---|---|
| 3,280,817 A | 10/1966 | Jorgensen et al. |
| 5,497,778 A | 3/1996 | Hon |
| 5,584,297 A | 12/1996 | Bodo et al. |
| 6,238,349 B1 * | 5/2001 | Hickey ........................ 600/486 |

* cited by examiner

*Primary Examiner*—George R. Evanisko
(74) *Attorney, Agent, or Firm*—Michael Best & Friedrich LLP

(57) ABSTRACT

A method and apparatus for determining A, C, and V waves in an atrial pressure waveform. The method includes the acts of establishing a time reference based on R waves in an ECG. A first interval in the an atrial pressure waveform between a first point offset ahead of a first R wave and a second point offset behind the first R wave is determined. The highest peak within the first interval is then identified. This peak is the A wave. Once the A wave is identified, a second R wave in the ECG, ahead of the first R wave, is identified. A second interval in the atrial pressure waveform that extends from the second point to a third point is established. The third point is positioned at a distance ahead of the second point equal to a percentage of the interval from the second point to a location behind the second R wave. The highest peak in the second interval is the V wave. After identifying the V wave, a third interval in the atrial pressure waveform is established. The third interval extends from the highest peak in the first interval to a fourth point. The fourth point is positioned at a distance ahead of the highest peak in the first interval (the A wave) equal to a second percentage of the distance between the highest peak in the first interval and the highest peak in the second interval (the V wave). The C wave is the highest peak in the third interval.

13 Claims, 3 Drawing Sheets

METHOD OF AND APPARATUS FOR IDENTIFYING A PORTION OF A WAVEFORM REPRESENTING A PHYSIOLOGICAL EVENT

RELATED APPLICATIONS

This applications is a division and claims priority under 35 U.S.C. §§120 and 121 to the filing date of co-pending U.S. patent application Ser. No. 09/474,592 filed Dec. 29, 1999.

BACKGROUND OF THE INVENTION

The present invention relates to a method and apparatus for interpreting medical data and particularly to the identification of particular waves in an atrial pressure waveform using an ECG (electrocardiogram).

The human heart receives blood from the veins and propels it into and through the arteries. The heart has two parallel and independent systems, each consisting of an atrium and a ventricle. From their anatomical positions, the right atrium and right ventricle are known as the right heart and the left atrium and left ventricle are known as the left heart. Blood from the body returns to the right atrium through two large veins, the superior and inferior venae cavae. Return of venous blood to the right atrium takes place during the entire heart cycle of contraction and relaxation. Return of venous blood to the right ventricle occurs only during the relaxation part of the heart-pumping cycle, called diastole. Near the end of diastole, the right atrium contracts and completes the filling of the right ventricle with blood. Contractions of the right ventricle expel the blood through the pulmonary arteries into the capillaries of the lung, where the blood receives oxygen. From the lung capillaries, the blood then empties into the pulmonary veins, and in turn into the left atrium. Return of blood from the pulmonary veins to the left atrium and left ventricle proceeds in a similar manner as the return of blood from the venae cavae to the right heart cavities. Contraction of the left ventricle propels the blood into the aorta. From there, blood is distributed to all arteries of the body, including the coronary arteries, which supply the heart muscle.

Contraction of the left and right ventricles occurs simultaneously, and is called systole. The blood forced from the ventricles during systole is prevented from returning to the ventricles during diastole by valves at the openings of the aortic and pulmonary arteries. These valves consist of three semilunar (half-moon-shaped) flaps of membrane. The flaps are curved in the direction of blood flow and open readily in response to pressure in that direction. When the original pressure subsides, back pressure forces the edges of the flaps together. The tricuspid valve, situated between the right atrium and right ventricle, is composed of three triangular flaps, and the bicuspid or mitral valve, between the left atrium and left ventricle, has two such flaps. The flaps of the mitral valve remain open until the left ventricle fills with blood. When the left ventricle begins to contract, the pressure of the pumped blood closes the mitral valve.

The rhythmic beating of the heart is maintained by an orderly series of electrical discharges originating in the sinus node of the right atrium. The discharges proceed through the atrioventricular node and a bundle of neuromuscular fibers (known as the bundle of His) to the ventricles. By attaching electrodes to various parts of the body, a record of the electrical discharges can be obtained. This record is called an electrocardiogram, or ECG.

Prominent parts of an ECG are the P wave, a deflection caused by the current originating in the atrium; the QRS complex, which is caused by the electrical activity of the ventricles as they contract; and the T wave, which is caused by relaxation of the ventricles. These changes in electrical activity may, in general, be sensed using probes or electrodes attached to the exterior of the body. The fluid pressure of blood in the atrium (the "atrial pressure waveform") may be sensed by attaching a pressure sensor or pressure transducer to a probe (such as a catheter), and positioning that probe in the atrium. Like a standard ECG, an atrial pressure waveform has several prominent parts and these parts can be associated with or related to the prominent parts of the ECG. The prominent parts of the atrial pressure waveform include an A wave. An A wave is caused by atrial systole and follows the P wave inscribed on the ECG. The A wave has a descent X that follows this initial positive deflection and is often interrupted by a small positive deflection called the C wave, which occurs when the tricuspid valve closes. At the lowest point of the descent X, complete atrial relaxation has occurred and pressure in the right atrium begins to rise again with atrial refilling. The rise in atrial pressure during ventricular systole is called the V wave. The V wave reaches its peak prior to the opening of the tricuspid valve. The descent Y of the V wave occurs as the tricuspid valve opens and the right atrium empties into the right ventricle. Pressure in the pulmonary artery (the "pulmonary artery wedge pressure") normally has a waveform similar to the waveform for the pressure in the left atrium. Although, the waveform for the pulmonary artery is delayed in transmission through the capillary vessels. A normal wedge pressure waveform has clear A and V waves, which may be detected by persons trained in reading ECGs. Descents X and Y are also clear, provided the pressure tracing is not overdamped. However, C waves are often not visible in the waveform.

Detecting the occurrence of A, V, and C waves is important in determining the maximum pressure present in the atrial and pulmonary veins and to identify the presence of prolapsed or calcified heart valves. While manual techniques exist to find these waves, they are not completely satisfactory, and automated techniques for finding C waves are not generally available. Accordingly, there is a need for improved methods of determining C waves in an atrial pressure waveform.

SUMMARY OF THE INVENTION

The present invention provides a method of determining A, C, and V waves. The method includes the acts of establishing a time reference based on R waves in an ECG. Using the R waves as a reference, a first interval in the atrial pressure waveform between a first point offset a predetermined amount ahead of a first R wave and a second point offset a predetermined amount behind the first R wave is determined. The highest peak within the first interval is then identified. This peak is the A wave.

Once the A wave is identified, a second R wave in the ECG, subsequent in time to the first R wave, is identified. Once the second R wave is determined, a second interval in the atrial pressure waveform that extends from the second point to a third point is established. The third point is positioned at a distance ahead (subsequent in time) of the second point equal to a percentage of the interval from the second point to a predetermined amount behind the second R wave. The highest peak in the second interval is the V wave.

After identifying the V wave, a third interval in the atrial pressure waveform is established. The third interval extends from the highest peak in the first interval to a fourth point.

The fourth point is positioned at a distance ahead of the highest peak in the first interval (the A wave) equal to a second percentage of the distance between the highest peak in the first interval and the highest peak in the second interval (the V wave). The C wave is the highest peak in the third interval. This same process may be repeated across the different R waves in the ECG to determine the A, C, and V waves for different "heart beats" or cardiac cycles.

As is apparent from the above, it is an advantage of the present invention to provide a method of determining or identifying the A, C, and V waves in a waveform. Other features and advantages of the present invention will become apparent by consideration of the detailed description and accompanying drawings.

DETAILED DESCRIPTION

Figure 1:
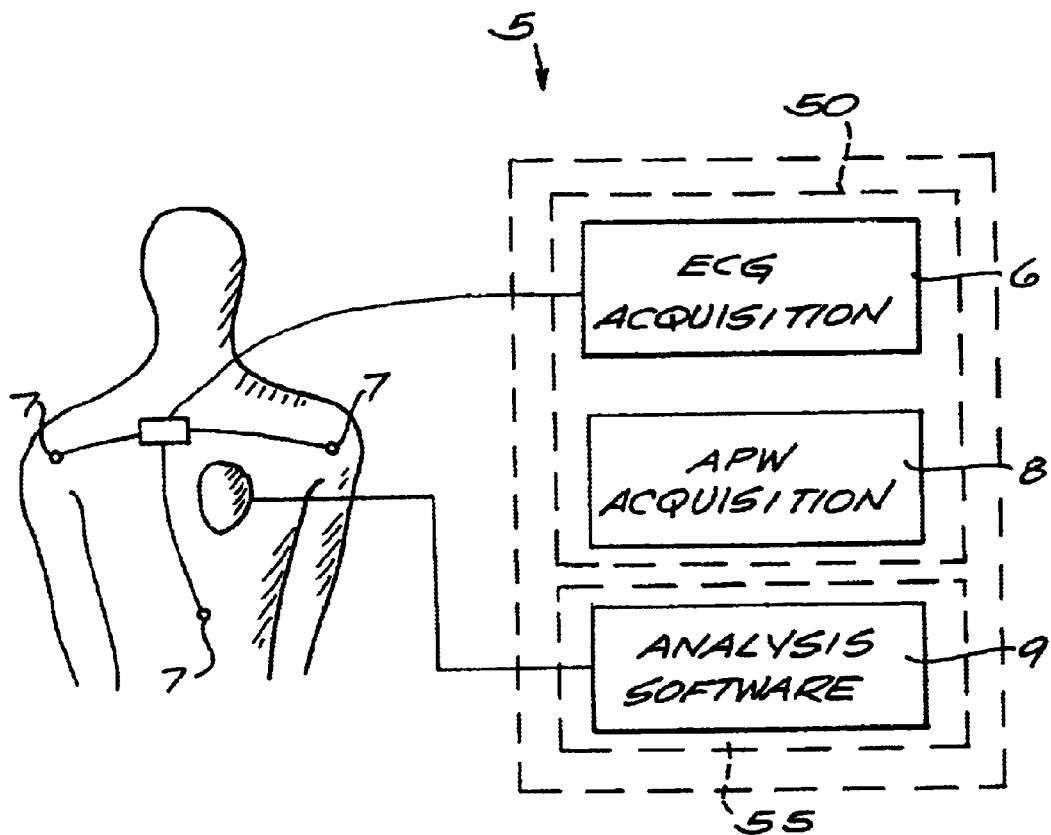
FIG. 1 is a schematic diagram of an apparatus embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates an apparatus 5 for acquiring ECG and atrial pressure waveforms that embodies the invention. While the apparatus 5 is shown as a single unit, it may be separated into discrete components that operate generally independent of the others. The apparatus 5 includes an acquisition module 50 having an ECG acquisition circuit 6. The EGG acquisition circuit 6, in the usual application, is externally connected to the patient through leadwires and electrodes 7 attached to the patient's skin. The invention, however, is equally applicable to EGG's that are acquired in other ways, e.g., through electrodes placed directly on the heart, through transesophageal monitoring, etc.

The acquisition module 50 also includes an atrial pressure waveform acquisition circuit 8 (APWAC). Typically, the APWAC is connected to a pressure sensor or transducer that is positioned in the right atrium of the patient's heart during a cardiac catheterization procedure.

The apparatus 5 also includes an analysis module 55 connected to the acquisition module 50. The analysis module 55 includes analysis software 9 that provides a means for identifying at least a portion of the APW atrial pressure waveform using the ECG waveform as a reference.

Figure 2:
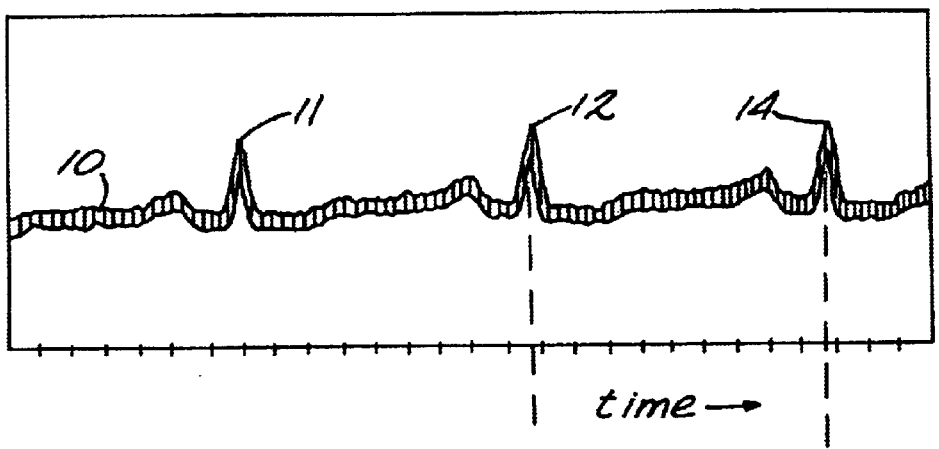
FIG. 2 is waveform diagram of an exemplary ECG with several R waves.
Figure 3:
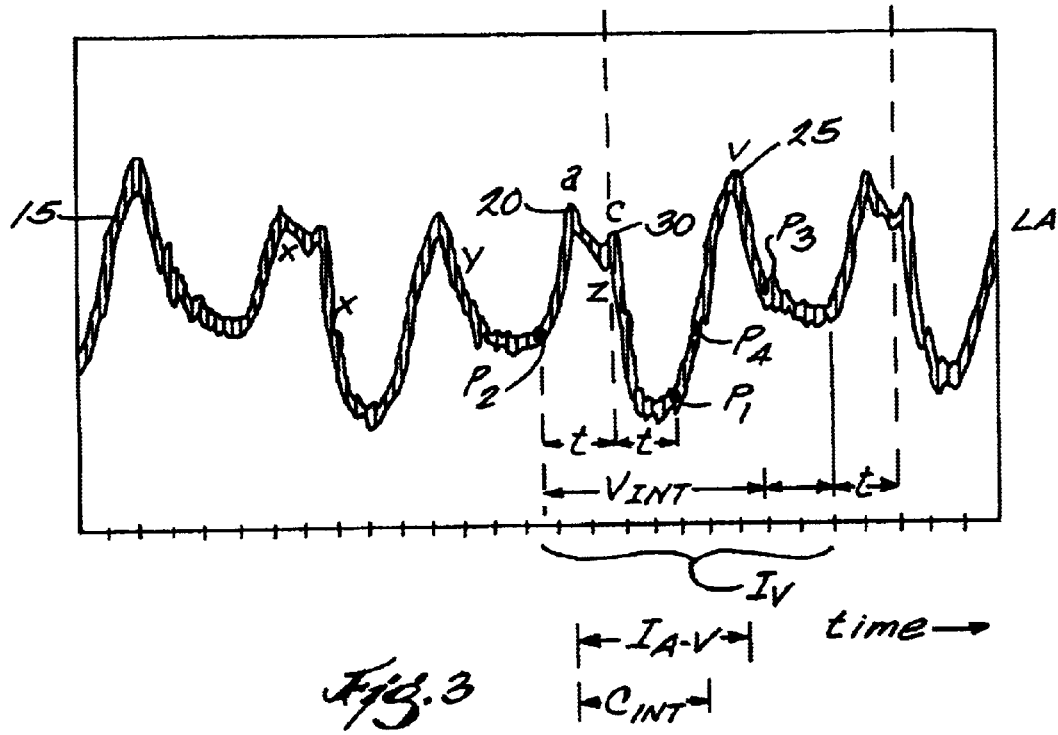
FIG. 3 is a diagram of an exemplary atrial pressure waveform.

FIG. 2 illustrates an exemplary ECG waveform 10 with three R waves 11, 12, and 14. FIG. 3 illustrates an exemplary atrial pressure waveform 15. The A, V, and C waves are determined or identified using the R waves of the ECG waveform 10 as a time reference. A waves are found by searching for the maximum peak pressure in an interval on the pressure waveform 15 from a point P1, located t seconds to the right of the R wave 12, to a point P2, located t seconds to the left of the R wave 12. The inventor has found that the value of the time-offset t should be based upon the heart rate of the patient. For heart rates less than 100 BPM (beats per minute), t should be set at about 150 ms. For heart rates between 100 and 150 BPM, t should be set at about 100 ms. For heart rates of 150 BPM or greater, t should be set at 75 ms. As shown in FIG. 3, an A wave 20 occurs in the interval between P1 and P2.

Once the A wave 20 has been found, the V wave may be found in the waveform 15 by searching for the maximum peak in an interval $V_{INT}$. The interval $V_{INT}$ extends from point P2 to point P3. Point P3 is positioned at a distance to the right of point P2 equal to 75% of an interval $I_V$ from point P2 to t seconds to the left of the R wave 14. As shown in FIG. 3, a V wave 25 occurs in the interval between P2 and P3.

The C wave may be found in the waveform 15 by searching for the highest peak following the A wave 20 in an interval $C_{INT}$. The interval $C_{INT}$ extends from about 25% to about 50% of the elapsed time (represented by an interval $I_{A-V}$) from the A wave 20 to the V wave 25 depending on the particular QRS of the reference ECG. In other words, the distance the interval $C_{INT}$ extends is dependent on the heart rate of the patient. As is known in the art, the Q of QRS refers to the ascent in the waveform before the occurrence of an R wave and the S refers to the descent in the waveform after the occurrence of an R wave. For high heart rates, the percentage of elapsed time from the A wave 25 to the V wave 25 is at the low end of the 25 to 50% range. For high heart rates, the percentage of elapsed time from the A wave 20 to the V wave 25 is at the high end of the 25 to 50% range. As can be seen by reference to FIG. 3, the highest wave in the interval $C_{INT}$ is a C wave 30.

Preferably, the procedure described above is implemented as software and used to analyze atrial pressure waveforms. In particular, it is envisioned that the improvements related to identifying the C wave in an atrial pressure waveform may be implemented in MAC-LAB Cardiac Catheterization software sold by GE Marquette Medical Systems, Inc.

Figure 4:
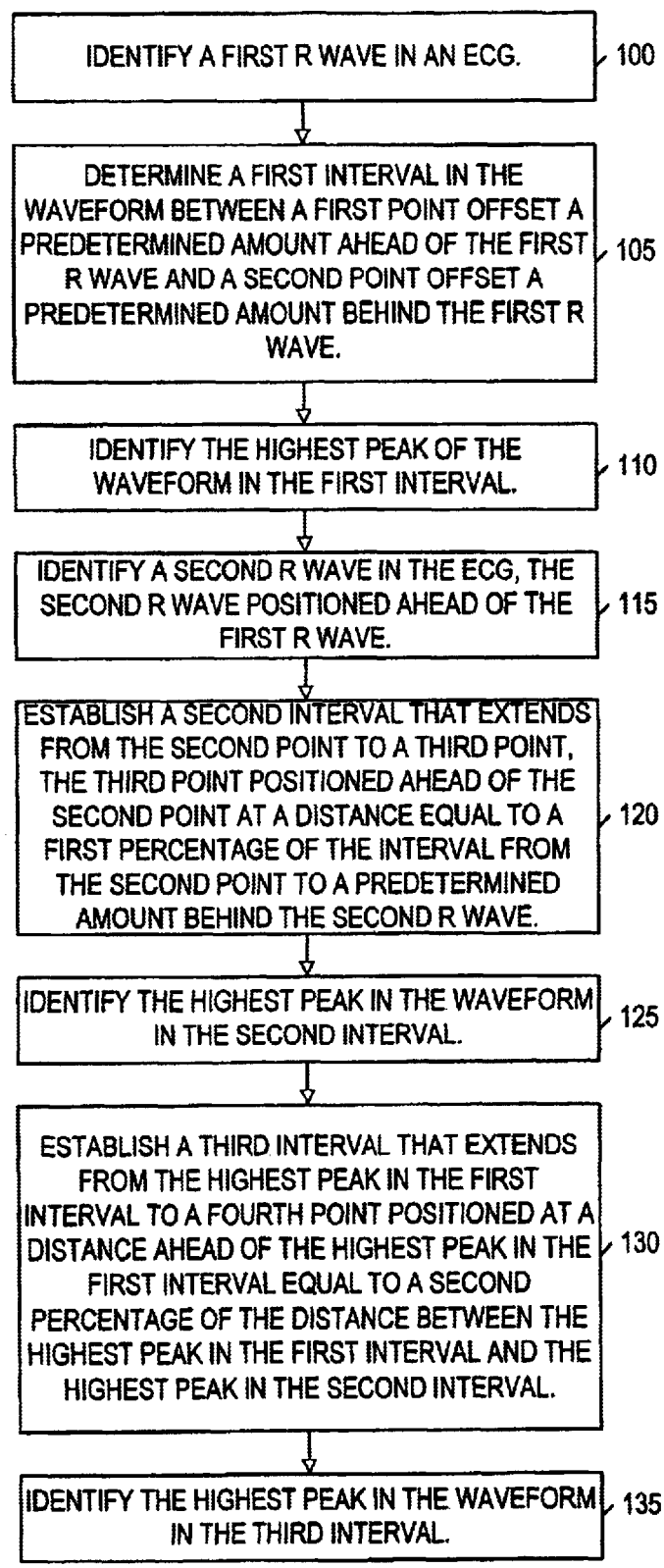
FIG. 4 is a flow chart of an exemplary method of identifying a portion of a waveform representing a physiological measurement.

FIG. 4 is a flow chart showing another exemplary method of operating the apparatus 5. The flow chart provides a method of identifying a portion of a waveform representing a physiological measurement. A number of the acts shown in FIG. 4 were described above with respect to the previously described embodiment.

With reference to FIG. 4, the method includes identifying a first R wave in an ECG (block 100), determining a first interval in the waveform between a first point offset a predetermined amount ahead of the first R wave and a second point offset a predetermined amount behind the first R wave (block 105), and identifying the highest peak of the waveform in the first interval (block 110). Once the highest peak in the first interval is identified, a second R wave positioned ahead of the first R wave is identified (block 115). After identifying the second R wave, the method includes establishing a second interval that extends from the second point to a third point (block 120). The third point is positioned ahead of the second point at a distance equal to a first percentage of the interval from the second point to a predetermined amount behind the second R wave. Once the second interval is established, the method includes identifying the highest peak in the waveform in the second interval (block 125). The method also includes establishing a third interval. The third interval extends from the highest peak in the first interval to a fourth point positioned at a distance ahead of the highest peak in the first interval equal to a second percentage of the distance between the highest peak in the first interval and the highest peak in the second interval (block 130). Once the third interval is established, the method includes identifying the highest peak in the waveform in the third interval (block 135).

As can be seen from the above, the invention provides a method for determining or identifying A, C, and V waves in an atrial pressure waveform.

Various features and advantages of the invention are set forth in the following claims.

What is claimed is:

1. A method of identifying an A wave in an atrial pressure waveform, the method comprising:

establishing a time reference based on R waves in an ECG;

determining a first interval in the atrial pressure waveform between a first point offset a positive amount ahead of a first R wave and a second point offset a predetermined amount behind the first R wave; and identifying the highest peak of the atrial pressure waveform in the first interval and designating the highest peak as the A wave.

2. A method as claimed in claim 1, wherein the ECG indicates a heart rate, and wherein the offsets of the first and second points are based on the heart rate.

3. A method as claimed in claim 2, wherein the offsets of the first and second points are equal to one another.

4. A method as claimed in claim 2, wherein the offsets of the first and second points are about 150 ms.

5. A method as claimed in claim 2, wherein the offsets of the first and second points are about 100 ms.

6. A method as claimed in claim 2, wherein the offsets of the first and second points are about 75 ms.

7. A method of identifying a wave in an atrial pressure waveform, the method comprising:

establishing a time reference based on R waves in an ECG;

determining a first interval in the atrial pressure waveform between a first point offset a predetermined amount ahead of a first R wave and a second point offset a predetermined amount behind the first R wave;

identifying the highest peak of the atrial pressure waveform in the first interval;

identifying a second R wave in the ECG ahead of the first R wave;

establishing a second interval that extends from the second point to a third point, the third point positioned at a distance ahead of the second point equal to a percentage of the interval from the second point to a predetermined amount behind the second R wave; and identifying the highest peak in the atrial pressure waveform in the second interval.

8. A method as claimed in claim 7, wherein the percentage is about 75 percent.

9. A method as claimed in claim 7, further comprising establishing a third interval that extends from the highest peak in the first interval to a fourth point positioned at a distance ahead of the highest peak in the first interval equal to a second percentage of the distance between the highest peak in the first interval and the highest peak in the second interval; and identifying the highest peak of the atrial pressure waveform in the third interval.

10. A method as claimed in claim 9, wherein the second percentage is from about 25 percent to about 50 percent.

11. A method of identifying a wave in a waveform, the method comprising:

identifying a first R wave in an ECG;

identifying an A wave in the waveform;

identifying a second R wave in the ECG, the second R wave positioned ahead of the first R wave;

identifying a V wave in the waveform;

establishing an interval that extends from the A wave to a point positioned at a distance ahead of the A wave that is a percentage of the distance between the A wave and the V wave; and identifying the highest peak in the waveform in the interval.

12. A method as claimed in claim 11, wherein the percentage is from about 25 percent to about 50 percent.

13. A method as claimed in claim 12, wherein the percentage is based on heart rate.

* * * * *

UNITED STATES PATENT AND TRADEMARK OFFICE
CERTIFICATE OF CORRECTION

PATENT NO.   : 6,690,968 B2
DATED        : February 10, 2004
INVENTOR(S)  : Claudio P. Mejia It is certified that error appears in the above-identified patent and that said Letters Patent is hereby corrected as shown below:

<u>Column 3,</u>
Line 49, delete "EGG's" and substitute "ECG's"

<u>Column 5,</u>
Line 21, add the word -- predetermined -- before the word "positive"

Signed and Sealed this

Twenty-ninth Day of June, 2004

JON W. DUDAS
*Acting Director of the United States Patent and Trademark Office*